United States Patent [19]

Brooks et al.

[11] 4,052,392
[45] Oct. 4, 1977

[54] 2-AMINO-4-CHLORO-6-(2'-HYDROXY-PHENOXY)-S-TRIAZINE

[75] Inventors: John Langshaw Brooks; David Crawford Eaton; Barry Williams, all of Manchester, England

[73] Assignee: Imperial Chemical Industries Limited, London, England

[21] Appl. No.: 671,547

[22] Filed: Mar. 29, 1976

[30] Foreign Application Priority Data

June 3, 1975 United Kingdom ............... 23922/75

[51] Int. Cl.² ........................................... C07D 251/42
[52] U.S. Cl. .................................................. 544/211
[58] Field of Search ..................... 260/249.5

[56] References Cited

U.S. PATENT DOCUMENTS 3,257,354 6/1966 Dexter et al. ................. 260/249.5 X Primary Examiner—John M. Ford
Attorney, Agent, or Firm—Cushman, Darby & Cushman

[57] ABSTRACT

The compound of the formula

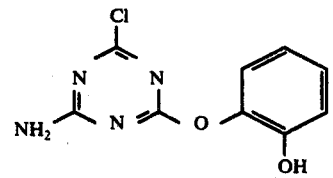

is exceptionally useful as an agent for increasing the bond strength between rubber and copper or its alloys.

1 Claim, No Drawings

2-AMINO-4-CHLORO-6-(2'-HYDROXY-PHENOXY)-S-TRIAZINE

This invention relates to a new heterocyclic compound and to its use in the bonding of rubber to copper and alloys thereof.

U.S. Pat. No. 3,894,903 describes the use of certain s-triazine compounds as additives to vulcanisable rubber compositions which are to be bonded to copper and to alloys thereof, and states that the preferred triazine compounds have the formula:

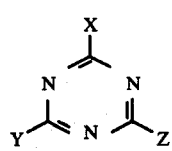
(1)

in which X is an optionally substituted m-hydroxyphenoxy or a m-hydroxyanilino group, and Y and Z, which may be the same or different, are each a group X or an amino, methylamino or chloro group, and especially those in which X is a m-hydroxyphenoxy group optionally containing a further hydroxyl group, Y is a chlorine atom and Z an amino group.

It has now been found that the compound of formula (1) in which X is Cl, Y is $NH_2$ and Z is o-hydroxyphenoxy gives extremely good bonds which are superior in bond strength to those from the compounds stated to be preferred in the above specification.

The new triazine compound can be obtained by reacting cyanuric chloride first with 1 mole of ammonia and then with 1 mole of catechol, in the presence of acid binding agents.

The triazine compound should be used in amount at least 0.1%, and preferably between 1 and 5%, of the weight of rubber. It is not necessary that the triazine compound should be distributed throughout the rubber but only that it should be present in adequate amount in the region of the rubber/metal interface. Thus comparatively small amounts of a rubber containing the triazine compound may be used as a bonding agent at the point of contact between metal and a rubber free from triazine compound.

Vulcanisation may be carried out by heating the composite article to a temperature conventionally used for vulcanising the vulcanisable rubber composite concerned. The vulcanisable rubber composition will normally contain a vulcanising agent such as sulphur or a sulphur donor for example N,N'-dithio-bis(hexahydro-2H-azepinone-3), 4,4'-dithiomorpholine or bis-[(diethyl)thiophosphoryl]trisulphide and a vulcanisation accelerator for example benzothiazylsulphenamides such as benzothiazyl-2-cyclohexyl sulphenamide, 2-(morpholinothio) benzothiazole, benzothiazyl-2-dicyclohexylsulphenamide, and N-t-butyl-2-benzothiazolesulphenamide, 2-mercaptobenzothiazole, 2-mercaptobenzothiazyl-disulphide, diarylguanidines, thiurams and dithiocarbamates.

The vulcanisable rubber composition may if desired contain other conventional rubber adjuvants such as antioxidants, antiozonants, fillers, reinforcing agents, pigments, processing oils and acccelerator activators such as zinc oxide and stearic acid and also ingredients used in other bonding systems such as formaldehyde generators.

The invention is illustrated but not limited by the following Examples in which all parts and percentages are by weight unless otherwise stated.

EXAMPLE 1

A suspension of 36.9 parts of cyanuric chloride in 250 parts of water at 0°–5° C was prepared. To the stirred suspension at this temperature were added separately over about 30 minutes a solution of ammonia (3.4 parts) in water (80 parts) concurrently with a solution of sodium hydroxide (8.0 parts) in water (80 parts). Stirring was continued at 0°–5° C for about 90 minutes after completion of the addition. The temperature of the mixture was then increased to 35° C and solutions of catechol (22 parts) in water (180 parts) and sodium hydroxide (8 parts) in water (70 parts) were added with stirring at this temperature over about 40 minutes. Stirring was continued for about 1 hour at 35° C when the reaction reached neutrality. The reaction mixture was cooled to 10° C and the product isolated by filtration, washed with water and dried. 2-amino-4-chloro-6-(2'-hydroxyphenoxy)-s-triazine was thereby obtained as an off-white powder of indefinite melting point due to decomposition, analysing for carbon 43.2%, hydrogen 2.6%, nitrogen 23.2% and chlorine 14.3%. ($C_9H_7ClN_4O_2$ requires carbon 45.3%, hydrogen 2.9%, nitrogen 23.5% and chlorine 14.9%).

EXAMPLE 2

A vulcanisable rubber composition was prepared on a two roll mill from the following ingredients

| | |
|---|---|
| Natural rubber smoked sheets | 100 |
| Zinc oxide | 10 |
| Stearic acid | 3 |
| High Abrasion Furnace Carbon Black | 45 |
| Processing oil | 4 |
| N-dicyclohexyl-2-benzothiazyl sulphenamide | 0.7 |
| Sulphur | 4 |
| Antioxidant (acetone/diphenylamine condensate) | 1 |
| 2-amino-4-chloro-6-(2'-hydroxyphenoxy)-s-triazine | 2 |

Samples measuring approximately 1¼inch × 7/16 inch × 7.3 mm were taken from the above composition and a length of brass-coated steel cord was sandwiched between two of the samples.

The resultant sandwich was placed in a mould, and press cured for 30 minutes at 150° C. After removal from the mould the resultant block, which measured 1¼ × ½ × ½ inch, was cut into two across the cord and the force required to pull the cord out of the rubber measured.

Force required to pull cord from 1¼ inch long block

| | |
|---|---|
| Without additive | 50 kg |
| With additive | 66 kg |

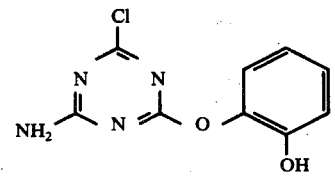

What we claim is:
1. The compound of the formula: